(12) United States Patent
Huter et al.

(10) Patent No.: US 6,645,220 B1
(45) Date of Patent: *Nov. 11, 2003

(54) EMBOLIC PROTECTION SYSTEM AND METHOD INCLUDING AND EMBOLIC-CAPTURING FILTER

(75) Inventors: Benjamin C. Huter, Temecula, CA (US); Scott J. Huter, Temecula, CA (US); Kent B. Stalker, San Marcos, CA (US)

(73) Assignee: Advanced Cardiovascular Systems, Inc., CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/475,600

(22) Filed: Dec. 30, 1999

(51) Int. Cl.⁷ .............................................. A61M 29/00

(52) U.S. Cl. ..................................................... 606/200

(58) Field of Search .............................. 606/200, 191, 606/194, 159, 127, 167, 108, 1; 623/1.15

(56) References Cited

U.S. PATENT DOCUMENTS

| | | | |
|---|---|---|---|
| 4,723,549 A | 2/1988 | Wholey et al. | |
| 4,997,435 A | 3/1991 | Demeter | |
| 5,100,425 A | 3/1992 | Fischell et al. | |
| 5,158,548 A | 10/1992 | Lau et al. | |
| 5,437,632 A | 8/1995 | Engleson | |
| 5,814,064 A | 9/1998 | Daniel et al. | |
| 5,827,324 A | 10/1998 | Cassell et al. | |
| 5,846,251 A | 12/1998 | Hart | |
| 5,911,734 A | 6/1999 | Tsugita et al. | |
| 5,980,532 A | * 11/1999 | Wang | 606/192 |
| 5,980,555 A | 11/1999 | Barbut et al. | |
| 5,989,281 A | 11/1999 | Barbut et al. | |
| 6,007,557 A | * 12/1999 | Ambrisco et al. | 606/159 |
| 6,171,327 B1 | * 1/2001 | Daniel et al. | 606/159 |
| 6,277,139 B1 | * 8/2001 | Levinson et al. | 606/127 |

OTHER PUBLICATIONS

US 6,348,062, 2/2002, Hopkins et al. (withdrawn)*

Pub. No.: US 2002/0022858 A1, "Vascular Device For Emboli Removal Having Suspension Strut and Methods of Use" Pub. Date: Feb. 21, 2002.*

* cited by examiner

Primary Examiner—David O. Reip
Assistant Examiner—(Jackie) Tan-Uyen T. Ho
(74) Attorney, Agent, or Firm—Fulwider Patton Lee & Utecht, LLP

(57) ABSTRACT

A system used in a blood vessel when an interventional procedure is being performed in a stenosed or occluded region to capture any embolic material which may be created and released into the bloodstream during the procedure. The system includes an emboli-capturing filter which is capable of occluding a blood vessel distal to an interventional procedure site, passing the blood to enable blood to flow past the occlusion, and filtering the blood to capture and retain embolic material which may be released into the blood during a therapeutic interventional procedure. The emboli-capturing filter includes an expandable member which is capable of projecting from a guiding catheter so as to be deployed distal to the interventional procedure site to filter the blood. The expandable member is also capable of being retracted into the guiding catheter to capture and retain any released embolic material. The expandable member is further capable of being expanded distal to the area of treatment at the interventional procedure site for occluding the blood vessel. The expandable member may also include a plurality of openings for enabling blood to pass therethrough while preventing emboli from passing therethrough.

54 Claims, 3 Drawing Sheets

EMBOLIC PROTECTION SYSTEM AND METHOD INCLUDING AND EMBOLIC-CAPTURING FILTER

BACKGROUND OF THE INVENTION

The present invention relates generally to a system which can be used when an interventional procedure is being performed in a stenosed or occluded region of a blood vessel to capture any embolic material that may be created and released into the bloodstream during the procedure. The system of the present invention is particularly useful when performing balloon angioplasty, stenting procedures, laser angioplasty or atherectomy in critical vessels, such as the carotid arteries, where the release of embolic debris into the bloodstream can occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, quite often particles are not fully vaporized and enter the bloodstream. Likewise, emboli may enter the bloodstream as well.

When any of the above-described procedures are performed in the carotid arteries, the release of emboli into the circulatory system can be extremely dangerous to the patient. Debris that is carried by the bloodstream to distal vessels of the brain can cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of a filter or trap downstream from the treatment site to capture embolic debris before it reaches the smaller blood vessels downstream. However, there have been problems associated with filtering systems, particularly during the expansion and collapsing of the filter within the body vessel. If the filtering device does not have a suitable mechanism for closing the filter, there is a possibility that trapped embolic debris can backflow through the open end of the filter and enter the blood-stream as the filtering system is being collapsed for removal from the patient. In such a case, the act of collapsing the filter device may actually squeeze trapped embolic material through the opening of the filter. The need for existing filters to be deployed in the full flow stream of the vessel without alternative paths for embolus free blood to supply the brain may result in deformation or incomplete deployment of the filter. In other instances, the rate of blood percolating through the filtering material may be slower than the normal blood flow which can either result in inadequate blood flow or promote clogging of the filter. If a filter should become clogged when in use in the carotid arteries, blood flow could be diminished to the vessels leading to the brain. While the brain may be capable of functioning for a very short period of time without sufficient blood flow, blood stoppage of more than thirty to forty seconds could cause the patient to experience a seizure or transient ischemic attacks. If the physician administering the procedure is unaware that the filtering device is clogged and that there is little or no blood flowing to the brain, the injury to the patient can be as devastating as if an emboli itself had caused blockage of the cerebral arteries.

What has been needed is a reliable system and method for treating stenosis in blood vessels which prevent the risk of releasing embolic debris into the bloodstream that can cause blockage in vessels at downstream locations. The system and method should be capable of filtering any embolic debris which may be released into the bloodstream during the treatment, and yet allow a sufficient amount of oxygenated blood to flow past the filtering device to supply vital organs downstream from the treatment site. The system and method should be relatively easy for a physician to use and should provide a failsafe filtering system which removes all embolic debris from the bloodstream. Moreover, such a system should be relatively easy to deploy and remove from the patient's vasculature. The inventions disclosed herein satisfy all of these needs.

SUMMARY OF INVENTION

The present invention provides a system and method for capturing and retaining embolic debris from a blood vessel which may be created during the performance of a therapeutic interventional procedure, such as a balloon angioplasty or stenting procedure, in order to prevent the embolic debris from lodging and blocking blood vessels downstream from the interventional site. The present invention is particularly useful while performing an interventional procedure in vital arteries, such as the carotid arteries, in which critical downstream blood vessels can become blocked with embolic debris, including the main blood vessels leading to the brain or other vital organs. As a result, the present invention provides the physician with a higher degree of confidence that any and all embolic debris is being collected and removed from the blood vessel when performing high-risk interventional procedures.

The present invention occludes the blood vessel at a location distal to the area of treatment in the interventional procedure site, passes the blood therethrough to enable blood to flow past the occlusion, and filters the blood to capture and retain any embolic debris which may be created during the interventional procedure.

In the present invention, the system includes an emboli-capturing filter with an expandable member to occlude a blood vessel and to capture and retain embolic material, and a plurality of openings in the expandable member to enable the blood to flow past the occlusion. The emboli-capturing filter of the present invention directs the blood flow through the area where the interventional procedure is to be performed and through the filter located distal to the interventional site, which is designed to capture and retain any friable plaque deposits. Additionally, the present invention allows blood to flow past the filter to provide a continuous stream of blood to the organs located downstream.

In a particular embodiment of the present invention, the emboli-capturing filter includes an expandable member which can be deployed within the blood vessel to prevent blood flow past the expandable member, for occluding the blood vessel at a location distal to the interventional procedure site. The expandable member may further include a plurality of openings which may be formed therein, which are adapted to pass blood therethrough while preventing embolic material from passing therethrough. The plurality of openings in the expandable member may be formed by a laser or other device, and may be formed in any of a plurality of shapes and sizes. The expandable member also includes an open proximal end and a plurality of openings therein for enabling the blood to be directed therethrough. The embolic protection system in which the expandable member may be used may include a guiding catheter which includes an elongated catheter body which has a proximal and distal end along with a main lumen which extends through the catheter body. The emboli protection system further includes an emboli-capturing filter which may project from the distal end of the guiding catheter. The emboli-capturing filter further includes the expandable member which extends from the distal end of the guiding catheter and which is adapted to project from and retract into the guiding catheter. The expandable member is adapted to be expanded to occlude the blood vessel, and to be contracted to capture and retain embolic material. As a result even though the expandable member occludes the blood vessel, the blood will continue to flow through the expandable member and out the openings therein. The blood flowing through the expandable member directs any embolic debris distal of the interventional site. The expandable member is adapted to capture and retain embolic material which may be released into the blood in the blood vessel during the interventional procedure.

Other features and advantages of the present invention will become more apparent from the following detailed description of the preferred embodiments of the invention, when taken in conjunction with the accompanying exemplary drawings.

DETAILED DESCRIPTION OF THE PREFERRED EMBODIMENTS

Figure 1:
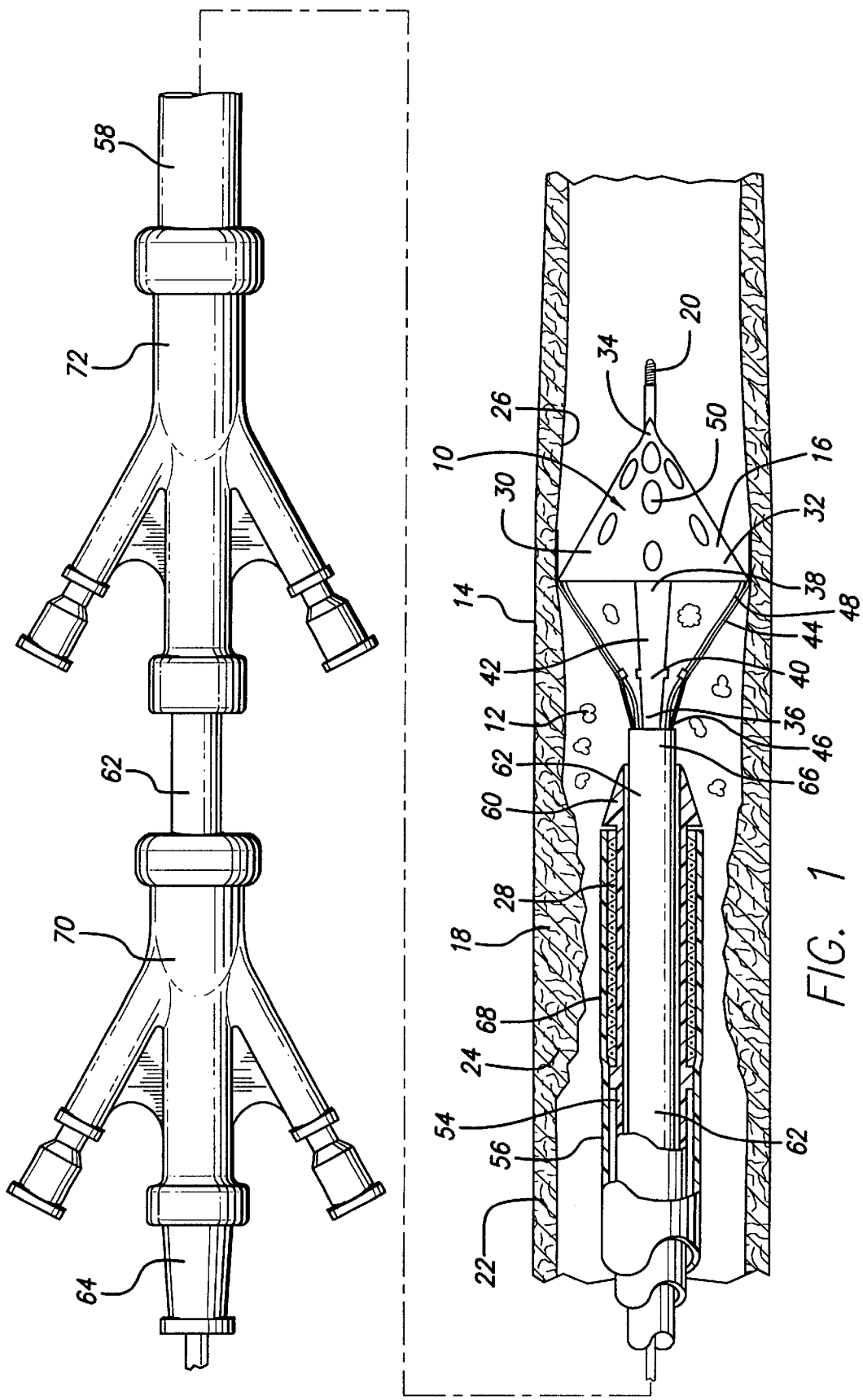
FIG. 1 is an elevational view, partially in section, depicting the embolic protection system of the present invention disposed within the internal carotid artery of the patient, in an embodiment of a guiding catheter and an emboli-capturing filter including an expandable member for directing blood and embolic material therethrough and for capturing and retaining embolic material.

The present invention is directed to an improved system and method for efficiently and effectively capturing and retaining embolic debris which may be released into the bloodstream when performing an interventional procedure in a blood vessel. The preferred embodiments of the improved system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Referring now to the drawings, wherein like reference numerals denote like or corresponding parts throughout the drawing figures, and particularly to FIGS. 1–6, an embolic protection system 10 is provided for capturing and retaining embolic material 12 which may be released into the blood in a blood vessel 14 during a therapeutic interventional procedure. The embolic protection system 10 comprises an emboli-capturing filter 16. The emboli-capturing filter 16 is adapted to be guided to and deployed within the blood vessel 14 at a location distal to an area of treatment 18 by a guide wire 20. It is further adapted to occlude the blood vessel 14 at a location distal to an interventional procedure site in the area of treatment 18, to pass the blood to enable the blood to flow past the occlusion, to capture and retain embolic material 12 which may be released into the blood in the blood vessel 14 during the interventional procedure, and to enable retraction of the emboli-capturing filter 16 and retention of the captured embolic material 12 therein. Additional details regarding the particular structure and shape of the various elements making up the emboli-capturing filter 16 are provided below.

The embolic protection system 10 as shown in FIG. 1 may be placed within the carotid artery 22 or other blood vessel of the patient, and may be guided into position by the guide wire 20. The carotid artery 22 may have an area of treatment 18 wherein atherosclerotic plaque 24 has built up against the inside wall 26 which decreases the diameter of the internal carotid artery 22. As a result, blood flow will be diminished through this area. As will be discussed below, the therapeutic interventional procedure may comprise implanting a self-expanding stent 28 in the area of treatment 18 to compress the build-up of plaque 24 of the stenosis against the inside wall 26, to increase the diameter of the occluded area 18 of the artery 30, and to help restore sufficient flow of blood to the downstream vessels leading to the brain. The self-expanding stent 28 not only helps increase the diameter of the occluded area, but may help prevent restenosis in the area of treatment 18.

The emboli-capturing filter 16 as illustrated in FIGS. 1–6 includes an expandable member 30. As can be seen in FIG. 1, the expandable member 30 may be deployed or expanded so as to make full contact with the walls 26 of the carotid artery 22 to occlude the blood vessel 14 and prevent the blood from flowing past the expandable member 30, and to direct the flow of blood flowing through the blood vessel 14 therethrough. The expandable member 30 is further adapted to be contractable. It includes a proximal end 32 which is open and a distal end 34 which direct the blood flowing through the blood vessel 14 therethrough. It is preferably generally conical-shaped.

The filter 16 may further include elements 36 for expansion and contraction of the expandable member 30. The elements 36 may include a plurality of outer membranes 38, each of which includes a proximal end 40 and a distal end 42 connected to the proximal end 32 of the expandable member 30. The expansion elements 36 may further include a plurality of spars 44, each of which includes a proximal end 46 and a distal end 48 connected to the open proximal end 32 of the expandable member 30.

Figure 2:
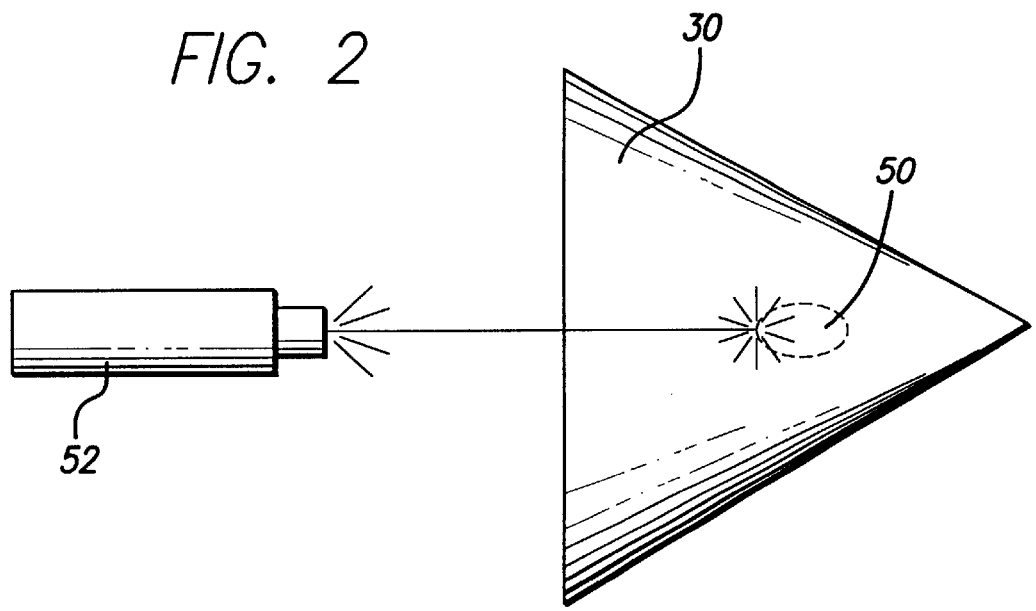
FIG. 2 is an elevational view of a laser forming an opening in an expandable member of the emboli-capturing filter.
Figure 3:
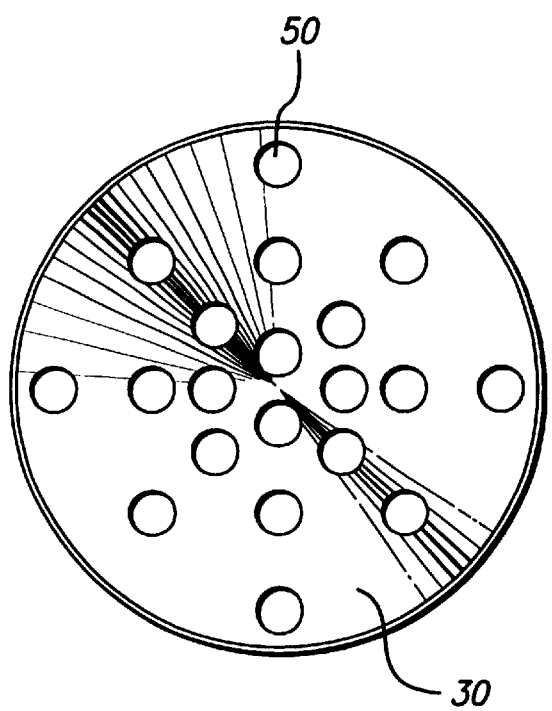
FIG. 3 is a front view of the expandable member including a first embodiment of a plurality of openings formed therein.
Figure 4:
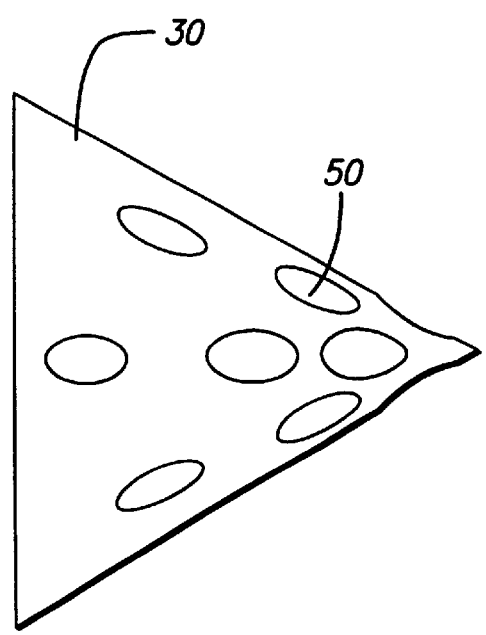
FIG. 4 is a side elevational view of another embodiment of the expandable member including the first embodiment of the plurality of openings formed therein.
Figure 5:
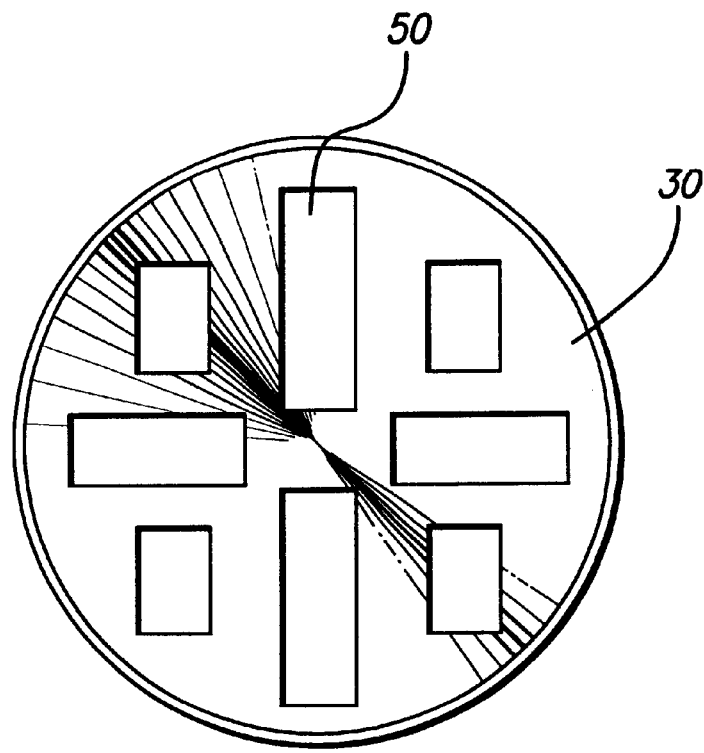
FIG. 5 is a front view of the expandable member including a second embodiment of a plurality of openings formed therein.
Figure 6:
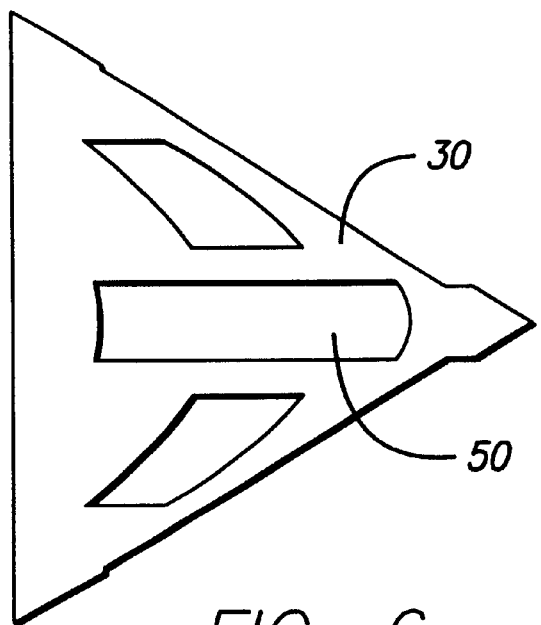
FIG. 6 is a side elevational view of the expandable member including the second embodiment of the plurality of openings formed therein.

The expandable member 30 may also have a plurality of openings or ports 50 which may be formed therein, to enable blood which is flowing through the blood vessel 14 and blocked by the expandable member 30 to flow therethrough, and to prevent embolic material 12 which may be released into the blood during the interventional procedure from passing therethrough. The plurality of openings 50 may be formed by a laser 52 as shown in FIG. 2, or by a heated rod. The plurality of openings 52 may also be formed in any of a plurality of shapes and sizes, as shown for example in FIGS. 3–6. The plurality of openings 50, when formed by the laser 52, are adapted to be formed so as to be smaller than a desired size for filtering particular embolic material 12, and to stretch upon expansion of the expandable member 30 to the desired size for filtering the particular embolic material 12. The plurality of sizes of the openings 50 may also be dependent upon the location of the openings 50 in the expandable member 30 relative to the size of the embolic material to be captured thereby, as for example with larger size openings towards the proximal end 32 of the expandable member 30 to filter larger embolic material 12. The expandable member 30 is preferably comprised of a mesh polymer material. The mesh polymer material of which the expandable member 30 is preferably comprised has mesh openings therein, the size of which is selectable dependent upon the size of the embolic material 12 to be filtered thereby. It may be formed for example by blow molding or dip molding over a mandrel.

As shown in FIG. 1, the embolic protection system 10 may further comprise a guiding catheter 54, which includes a central lumen 56, a proximal end 58, and a distal end 60. The guiding catheter 54 is adapted to enable the filter 16 to be retracted into the lumen 56 therein. The guiding catheter 54 is further adapted to carry interventional instruments such as the self-expanding stent 28 to the interventional procedure site at the area of treatment 18. The guiding catheter 54 includes an elongated shaft 62 which includes a proximal end 64 and a distal end 66 for delivering the interventional instruments (herein the stent 28 located near the distal end 66 of the elongated shaft 62) into the area of treatment 18. The guiding catheter 54 may also include a retractable sheath 68 for covering the self-expanding stent 28 until it is positioned at the treatment area 18, and for being retracted so as to release the self-expanding stent 28 at the treatment area 18. The guiding catheter 54 may further include a multi-arm adapter 70, such as a Tuohy-Borst adapter, attached to the sheath 68. The guiding catheter 54 may still further include a multi-arm adapter 72, such as a Tuohy-Borst adapter, attached to a proximal end 64 of the elongated shaft 62.

In forming a filter 16 comprising the expandable member 30 as shown in FIGS. 2–6 for use in the embolic protection system 10, the expandable member 30 may be formed by blow molding in a mold and cutting to shape or dip molding over a mandrel. It may be comprised of a mesh polymer material, and may be formed in a generally conical shape, with an open proximal end 32 and a distal end 34. The mesh polymer material of which the expandable member 30 may be formed has mesh openings therein, the size of which is selectable dependent upon the size of the embolic material 12 to be filtered thereby. In forming the plurality of openings 50 in the expandable member 30 for use in the embolic protection system 10, the plurality of openings 50 may be formed by a laser 52 as illustrated in FIG. 2, or by a heated rod. The plurality of openings 50 formed by the laser 52 are adapted to be formed to be smaller than the size desired for filtering particular embolic material 12 to be filtered thereby, and are further adapted to stretch upon expansion of the expandable member 30 to the particular filtering size desired. The plurality of openings 50 may further be so formed in any of a plurality of shapes and sizes as seen for example in FIGS. 3–6. The plurality of sizes of the openings 50 may also be dependent upon the location of the openings 50 in the expandable member 30.

In use of the embolic protection system 10 including the filter 16 as illustrated in FIG. 1, the embolic protection system 10 may be positioned in the patient's vasculature utilizing any one of a number of different methods. In one preferred method of positioning, the guiding catheter 54 and the emboli-capturing filter 16 therein may be placed in the blood vessel 14 by utilizing the guide wire 20 which is inserted into the patient's vasculature and manipulated by the physician to the area of treatment 18. Thereafter, once the guide wire 20 is in place, the emboli-capturing filter 16 may be moved into position distal to the area of treatment 18, and the guiding catheter 54 is in position at the area of treatment 18.

In the embodiment as shown in FIG. 1, once the catheter 54 is in position in the blood vessel 14, the emboli-capturing filter 16, including the expandable member 30 may project from the catheter 54 so as to be deployed distal to the distal end 60 of the catheter 54. The expandable member 30 may then expand to occlude the blood vessel 14 and block the flow of blood distal to the treatment area 18. The expansion of the expandable member 30 may be achieved by operation of the expansion elements 36 such that the spars 44 and the outer membranes 38 expand, enabling the expandable member 30 to expand.

Upon expansion of the expandable member 30, whereby the blood vessel 14 is occluded, the blood is forced to flow through the expandable member 30 and the openings 50 therein, for enabling the blood to flow past the occlusion.

In the embodiment of the invention illustrated in FIGS. 1–6, as seen in FIG. 1, once the system 10 is placed in the patient's vasculature, with the expandable member 30 positioned distal to the treatment area 18, the retractable sheath 68 of the guiding catheter 54 may be retracted through use of the adapter 76, releasing the self-expanding stent 28 to compress the build-up of plaque 24 in the treatment area 18. Any embolic material 12 which may be released into the blood during the therapeutic procedure may then be directed with the blood flow through the filter 16 including the openings 50 in the expandable member 30 for filtering thereof, to capture embolic material 12 which may be released into the blood in the blood vessel 14 during the interventional procedure.

After a sufficient time passes to allow any embolic material 12 released into the blood to be captured and retained in the expandable member 30 of the filter 16, the filter 16 may be retracted into the lumen 56 of the guiding catheter 54. The expandable member 30 may be contracted by the operation of the expansion elements 36 such that the spars 44 and the outer membranes 38 contract, enabling the expandable member 30 to contract. The guiding catheter 54, along with the expandable member 30 with the embolic material 12 captured and retained therein, may then be withdrawn from the blood vessel 14, leaving the stent 28 in position therein.

It should be appreciated that the particular embodiments of the filter 16 are capable of being positioned in the blood vessel 14. However, other forms of the filter 16 may be utilized with the present invention without departing from the spirit and scope of the invention. Additionally, while the filter 16 is shown as in various shapes in the embodiments herein, it can be formed in any one of a number of different shapes depending upon the construction desired.

The filter 16 of the present invention may be formed of conventional materials of construction. The expandable member 30 can be made out of relatively inelastic materials such as polyethylene, polyvinyl chloride, polyesters and composite materials. The various components may be joined by suitable adhesives such as acrylonitrile based adhesive or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the safety of performing interventional procedures by significantly reducing the risks associated with embolic material being created and released into the patient's bloodstream. Further modifications and improvements may additionally be made to the system and method disclosed herein without the departing from the scope of the invention. Accordingly, it is not intended that the invention be limited, except as by the appended claims.

What is claimed is:

1. A filter for capturing and retaining embolic material which may be released into a blood vessel during a therapeutic interventional procedure, comprising:

an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the expandable member further includes a longitudinal axis extending therealong, and the plurality of openings include longitudinal openings adapted to extend along the expandable member longitudinal axis, and aligned openings adapted to extend in alignment in the generally longitudinal direction at an angle relative to and symmetrical about the longitudinal axis, and wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material.

2. The filter of claim 1, wherein the expandable member is comprised of a mesh polymer material.

3. The filter of claim 2, wherein the mesh polymer material has mesh openings therein, and the size of the mesh openings in the mesh polymer material is dependent upon the size of the emboli to be filtered thereby.

4. The filter of claim 1, wherein the expandable member is adapted to be formed by blow molding thereof over a mandrel.

5. The filter of claim 1, wherein the expandable member is adapted to be formed by dip molding thereof over a mandrel.

6. The filter of claim 1, wherein the plurality of openings in the expandable member are adapted to be formed by a heated rod.

7. The filter of claim 1, wherein the plurality of openings in the expandable member are adapted to be formed in any of a plurality of shapes.

8. The filter of claim 1, wherein the plurality of openings are adapted to be formed in a plurality of sizes.

9. The filter of claim 8, wherein the plurality of sizes of the openings in the expandable member are adapted to be dependent upon the location of the plurality of openings in the expandable member relative to the size of embolic material to be captured thereby.

10. The filter of claim 8, wherein the plurality of expandable member opening sizes comprise larger size openings towards the expandable member proximal end, and smaller size openings towards the expandable member distal end.

11. The filter of claim 1, wherein the plurality of laser-formed openings in the expandable member are adapted to be formed in a pattern which is symmetrical along a longitudinal axis of the expandable member, and which is asymmetrical transverse to the longitudinal axis of the expandable member.

12. The method of claim 11, wherein the plurality of openings in the expandable member are adapted to be formed in any of a plurality of shapes, and wherein forming the plurality of openings further comprises forming the plurality of openings in any of a plurality of shapes.

13. A system for capturing and retaining embolic material which may be released into a blood vessel during a therapeutic interventional procedure, comprising:

a filter, adapted to be guided to and deployed within a blood vessel at a location distal to an interventional procedure site, to occlude the blood vessel at a location distal to the interventional procedure site, to pass the blood to enable blood to flow past the occlusion, to capture embolic material which may be released into the blood in the blood vessel during the therapeutic interventional procedure, and to enable retention of the captured emboli therein, including:

an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the art captured emboli therein, wherein the expandable member is generally conical-shaped, wherein the expandable member has a plurality of openings therein for enabling blood to pass therethrough while preventing emboli from passing therethrough, and wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material.

14. The system of claim 13, further comprising means for guiding and deploying the filter at the location distal to the interventional procedure site.

15. The system of claim 14, wherein the guiding means comprise a guide wire for guiding movement of the filter.

16. The system of claim 13, further comprising a guiding catheter having a lumen therein, wherein the filter is adapted to project from the guiding catheter for filtering the emboli, and the filter with the captured emboli retained therein is further adapted to be retracted into the lumen in the guiding catheter.

17. The system of claim 16, further comprising means for guiding and deploying the filter at the location distal to the interventional procedure site, wherein the guiding means are further adapted to enable the filter to be retracted into the guiding catheter lumen.

18. The system of claim 13, further comprising means for expanding and contracting the expandable member.

19. The system of claim 13, wherein the expandable member includes a proximal end and a distal end, wherein the proximal end is open.

20. The system of claim 13, wherein the expandable member is comprised of a mesh polymer material.

21. The system of claim 20, wherein the mesh polymer material has mesh openings therein, and the size of the mesh openings in the mesh polymer material is dependent upon the size of the emboli to be filtered thereby.

22. The system of claim 13, wherein the expandable member is adapted to be formed by blow molding thereof in a mold and cutting to shape.

23. The system of claim 13, wherein the expandable member is adapted to be formed by dip molding thereof over a mandrel.

24. The system of claim 13, wherein the plurality of openings in the expandable member are adapted to be formed by a heated rod.

25. The system of claim 13, wherein the plurality of openings in the expandable member are adapted to be formed in any of a plurality of shapes.

26. The system of claim 13, wherein the plurality of openings in the expandable member openings are adapted to be formed in any of a plurality of sizes.

27. The system of claim 26, wherein the plurality of sizes of the openings in the expandable member are adapted to be dependent upon the location of the plurality of openings in the expandable member relative to the size of embolic material to be captured thereby.

28. A method of forming a filter for capturing and retaining embolic material which may be released into a blood vessel during a therapeutic interventional procedure, wherein the filter comprises an expandable member, adapted to be expandable within the blood vessel at a location distal to the interventional procedure site so as to occlude the blood vessel and direct the blood flowing through the blood vessel therethrough, and further adapted to be contractable so as to capture the embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the expandable member further includes a longitudinal axis extending therealong, and the plurality of openings include longitudinal openings adapted to extend along the expandable member longitudinal axis, and aligned openings adapted to extend in alignment in the generally longitudinal direction at an angle relative to and symmetrical about the longitudinal axis, and wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material, wherein the method comprises;

forming the expandable member so as to be generally conical-shaped, including a proximal end which is open and a distal end; and forming a plurality of openings in the expandable member for enabling blood to pass therethrough while preventing emboli from passing therethrough, including forming longitudinal openings along the expandable member longitudinal axis, and forming aligned openings extending in alignment in the generally longitudinal direction at an angle relative to and symmetrical about the longitudinal axis, and including forming larger size openings towards the proximal end of the expandable member, and forming smaller size openings towards the distal end of the expandable member.

29. The method of claim 28, wherein the expandable member is comprised of a mesh polymer material, and wherein forming the expandable member further comprises forming the expandable member of mesh polymer material.

30. The method of claim 29, wherein the mesh polymer material has mesh openings therein, and the size of the mesh openings in the mesh polymer material is dependent upon the size of the emboli to be filtered thereby, and wherein forming the expandable member further comprises forming the expandable member with mesh openings selected to enable filtering of the emboli to be filtered thereby.

31. The method of claim 28, wherein the expandable member is adapted to be formed by blow molding in a mold and cutting to shape, and wherein forming the expandable member further comprises forming the expandable member by blow molding thereof over a mandrel.

32. The method of claim 28, wherein the expandable member is adapted to be formed by dip molding thereof over a mandrel, and wherein forming the expandable member further comprises forming the expandable member by dip molding thereof over a mandrel.

33. The method of claim 28, wherein the plurality of openings in the expandable member are adapted to be formed by a heated rod, and wherein forming the plurality of openings in the expandable member further comprises forming the plurality of openings by a heated rod.

34. The method of claim 28, wherein the plurality of openings in the expandable member are adapted to be formed in a plurality of sizes, and wherein forming the plurality of openings further comprises forming the plurality of openings in a plurality of sizes.

35. The method of claim 34, wherein the plurality of sizes of the openings in the expandable member are adapted to be dependent upon the location of the plurality of openings relative to the size of embolic material to be captured thereby and wherein forming the plurality of openings further comprises forming the plurality of openings in the plurality of sizes in the expandable member dependent upon the location of the plurality of openings relative to the size of embolic material to be captured thereby.

36. The method of claim 34, wherein the plurality of expandable member opening sizes comprise larger size openings towards the expandable member proximal end, and smaller size openings towards the expandable member distal end.

37. The method of claim 28, wherein the plurality of laser-formed openings in the expandable member are adapted to be formed in a pattern which is symmetrical along a longitudinal axis of the expandable member, and which is asymmetrical transverse to the longitudinal axis of the expandable member, and wherein forming the plurality of openings further comprises forming the plurality of openings in a pattern which is symmetrical along the longitudinal axis of the expandable member, and which is asymmetrical transverse to the longitudinal axis of the expandable member.

38. A method of capturing and retaining embolic material which may be released into a blood vessel during a therapeutic interventional procedure, in a system which comprises a filter, adapted to be guided to and deployed within a blood vessel at a location distal to an interventional procedure site, to occlude the blood vessel at a location distal to the interventional procedure site, to pass the blood to enable blood to flow past the occlusion, to capture embolic material which may be released into the blood in the blood vessel during the therapeutic interventional procedure, and to enable retention of the captured emboli therein, including an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, wherein the expandable member has a plurality of openings therein for enabling blood to pass therethrough while preventing emboli from passing therethrough, and wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material, wherein the method comprises:

positioning the filter in the interventional procedure site such that the generally conical-shaped expandable member is located within the blood vessel in the region at a location distal to the interventional procedure site;

expanding the expandable member within the blood vessel at the location distal to the interventional procedure site so as to occlude the blood vessel;

passing the blood through the expandable member;

performing the interventional procedure, which may release embolic material into the blood;

filtering the blood through the expandable member, so as to capture larger embolic material in the proximal larger size openings, and smaller embolic material in the distal smaller size openings, which may be released into the blood upon performing the interventional procedure;

contracting the expandable member; and retaining the captured emboli in the expandable member.

39. The method of claim 38, further comprising means for guiding and deploying the filter at the location distal to the interventional procedure site, wherein positioning further comprises guiding and deploying the filter at the location distal to the interventional procedure site.

40. The method of claim 38, further comprising a guiding catheter having a lumen therein, wherein the filter is adapted to project from the guiding catheter for filtering the emboli, and the filter with the captured emboli retained therein is further adapted to be retracted into the lumen in the guiding catheter, wherein positioning further comprises projecting the filter from the guiding catheter, and wherein retaining further comprises retracting the filter into the guiding catheter lumen.

41. The method of claim 38, further comprising means for expanding and contracting the expandable member, and wherein expanding further comprises expanding the expanding means and contracting further comprises contracting the expanding means.

42. The method of claim 38, wherein the expandable member further includes a proximal end and a distal end, and the proximal end is open, and wherein expanding further comprises expanding the proximal end of the expandable member.

43. The method of claim 38, wherein the expandable member has a plurality of openings therein for enabling blood to pass therethrough while preventing emboli from passing therethrough, and wherein passing further comprises passing the blood through the plurality of openings in the expandable member.

44. The method of claim 38, wherein the expandable member is comprised of a mesh polymer material, and wherein expanding further comprises expanding the mesh polymer material of which the expandable member is comprised.

45. The method of claim 38, wherein the expandable member is adapted to be formed by blow molding thereof over a mandrel, further comprising forming the expandable member by blow molding in a mold and cutting to shape.

46. The method of claim 38, wherein the expandable member is adapted to be formed by dip molding thereof over a mandrel, further comprising forming the expandable member by dip molding thereof over a mandrel.

47. A filter for capturing and retaining embolic material which may be released into a blood vessel during a therapeutic interventional procedure, comprising:
an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the plurality of openings in the expandable member are adapted to be formed in a plurality of sizes therein and wherein the expandable member includes a proximal end and a distal ends, and the plurality of openings include larger size openings towards the proximal end of the expandable member, adapted to filter larger embolic material, and smaller size openings towards the distal end of the expandable member, adapted to filter smaller embolic material.

48. A method of forming a filter for capturing and retaining embolic material which may be released into a blood vessel during a therapeutic interventional procedure, wherein the filter comprises an expandable member, adapted to be expandable within the blood vessel at a location distal to the interventional procedure site so as to occlude the blood vessel and direct the blood flowing through the blood vessel therethrough, and further adapted to be contractable so as to capture the embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the plurality of openings in the expandable member are adapted to be formed in a plurality of sizes therein, and wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material, wherein the method comprises;
forming the expandable member so as to be generally conical-shaped, including a proximal end which is open and a distal end; and
forming a plurality of openings in the expandable member in a plurality of sizes therein for enabling blood to pass therethrough while preventing emboli from passing therethrough, including forming larger size openings towards the proximal end of the expandable member, and forming smaller size openings towards the distal end of the expandable member.

49. A filter for capturing and retaining embolic material which may be released into a blood vessel during a therapeutic interventional procedure, comprising:
an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material.

50. A system for capturing and retaining embolic material which may be released into a blood vessel during a therapeutic interventional procedure, comprising:
a filter, adapted to be guided to and deployed within a blood vessel at a location distal to an interventional procedure site, to occlude the blood vessel at a location distal to the interventional procedure site, to pass the blood to enable blood to flow past the occlusion, to capture embolic material which may be released into the blood in the blood vessel during the therapeutic interventional procedure, and to enable retention of the captured emboli therein, including:

an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, wherein the expandable member includes a proximal end and a distal end, and the plurality of openings include larger size openings towards the proximal end of the expandable member, adapted to filter larger embolic material, and smaller size openings towards the distal end of the expandable member, adapted to filter smaller embolic material.

51. A method of forming a filter for capturing and retaining embolic material which may be released into a blood vessel during a therapeutic interventional procedure, wherein the filter comprises an expandable member, adapted to be expandable within the blood vessel at a location distal to the interventional procedure site so as to occlude the blood vessel and direct the blood flowing through the blood vessel therethrough, and further adapted to be contractable so as to capture the embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, and the plurality of openings include larger size openings towards the proximal end of the expandable member, adapted to filter larger embolic material, and smaller size openings towards the distal end of the expandable e member, adapted to filter smaller embolic material wherein the method comprises:

forming the expandable member so as to be generally conical-shaped, including a proximal end which is open and a distal end; and forming a plurality of openings in the expandable member for enabling blood to pass therethrough while preventing emboli from passing therethrough, including forming larger size openings towards the proximal end of the expandable member, and forming smaller size openings towards the distal end of the expandable member.

52. A method of capturing and retaining embolic material which may be released into a blood vessel during a therapeutic interventional procedure, in a system which comprises a filter, adapted to be guided to and deployed within a blood vessel at a location distal to an interventional procedure site, to occlude the blood vessel at a location distal to the interventional procedure site, to pass the blood to enable blood to flow past the occlusion, to capture embolic material which may be released into the blood in the blood vessel during the therapeutic interventional procedure, and to enable retention of the captured emboli therein, including an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, and includes a proximal end and a distal end, and the plurality of openings include larger size openings towards the proximal end of the expandable member, adapted to filter larger embolic material, and smaller size openings towards the distal end of the expandable member, adapted to filter smaller embolic material, wherein the method comprises:

positioning the filter in the interventional procedure site such that the generally conical-shaped expandable member is located within the blood vessel in the region at a location distal to the interventional procedure site;

expanding the expandable member within the blood vessel at the location distal to the interventional procedure site so as to occlude the blood vessel;

passing the blood through the expandable member;

performing the interventional procedure, which may release embolic material into the blood;

filtering the blood through the expandable member, so as to capture larger embolic material in the proximal larger size openings, and smaller embolic material in the distal smaller size openings, which may be released into the blood upon performing the interventional procedure;

contracting the expandable member; and retaining the captured emboli in the expandable member.

53. A filter for capturing and retaining embolic material which may be released into a blood vessel during a therapeutic interventional procedure, comprising:

an expandable member, adapted to be expandable within the blood vessel at a location distal to the interventional procedure site so as to occlude the blood vessel and direct the blood flowing through the blood vessel therethrough, and further adapted to be contractable so as to capture embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the plurality of openings in the expandable member are adapted to be formed in a plurality of sizes therein, and wherein the plurality of openings include larger size openings towards the proximal end of the expandable member, adapted to filter larger embolic material, and smaller size openings towards the distal end of the expandable member, adapted to filter smaller embolic material.

54. A method of forming a filter for capturing and retaining embolic material which may be released into a blood vessel during a therapeutic interventional procedure, wherein the filter comprises an expandable member, adapted to be expandable within the blood vessel at a location distal to the interventional procedure site so as to occlude the blood vessel and direct the blood flowing through the blood vessel therethrough, and further adapted to be contractable so as to capture the embolic material which may be released into the blood in the blood vessel during the therapeutic interventional procedure, and to retain the captured emboli therein, wherein the expandable member is generally conical-shaped, includes a proximal end which is open and a distal end, and has a plurality of openings therein for enabling blood to pass therethrough while preventing emboli from passing therethrough, wherein the plurality of openings in the expandable member are adapted to be formed in a plurality of sizes therein, and wherein the plurality of openings include larger size openings towards the proximal end of the expandable member, adapted to filter larger embolic material, and smaller size openings towards the distal end of the expandable member, adapted to filter smaller embolic material, wherein the method comprises;

forming the expandable member so as to be generally conical-shaped, including a proximal end which is open and a distal end; and forming a plurality of openings in the expandable member in a plurality of sizes therein for enabling blood to pass therethrough while preventing emboli from passing therethrough, so as to capture larger embolic material in the proximal larger size openings, and smaller embolic material in the distal smaller size openings.

* * * * *

UNITED STATES PATENT AND TRADEMARK OFFICE
CERTIFICATE OF CORRECTION

PATENT NO. : 6,645,220 B1  
DATED : November 11, 2003  
INVENTOR(S) : Benjamin C. Huter, Scott J. Huter and Kent B. Stalker It is certified that error appears in the above-identified patent and that said Letters Patent is hereby corrected as shown below:

Title page, Item [54] and Column 1, lines 2 and 3,
Title, delete "AND" and insert -- AN --; and delete "EMBOLIC-CAPTURING" and insert -- EMBOLI-CAPTURING --.

Column 13,
Line 57, delete "ends," and insert -- end, --.

Column 15,
Line 39, delete "e" after "expandable".

Signed and Sealed this

Thirteenth Day of April, 2004

JON W. DUDAS
*Acting Director of the United States Patent and Trademark Office*